United States Patent [19]

Seal

[11] Patent Number: 5,052,929
[45] Date of Patent: Oct. 1, 1991

[54] METHOD FOR CONSTRUCTING A CUSTOM ABUTMENT FOR USE IN ASSOCIATION WITH DENTAL IMPLANTS

[76] Inventor: D. Greg Seal, 6170 Sni-A-Bar Rd., Kansas City, Mo. 64129

[21] Appl. No.: 489,061

[22] Filed: Mar. 2, 1990

[51] Int. Cl.$^5$ .............................................. A61C 8/00
[52] U.S. Cl. ..................................... 433/173; 433/213
[58] Field of Search ............... 433/172, 173, 174, 175, 433/176, 207, 213; 420/509

[56] References Cited

U.S. PATENT DOCUMENTS

| | | | |
|---|---|---|---|
| 4,744,756 | 5/1988 | Ross | 433/173 |
| 4,806,306 | 2/1989 | Groll et al. | 433/207 |

*Primary Examiner*—Cary E. O'Connor
*Attorney, Agent, or Firm*—Allegretti & Witcoff, Ltd.

[57] ABSTRACT

A dental abutment, and method for using the dental abutment to manufacture a custom dental abutment for use in association with dental implants is disclosed. The abutment comprises an attaching means for attaching the abutment to an implant which is already in position in a patient's mouth along with a cuff, and a body. A custom dental abutment is manufactured by screwing the dental abutment tightly into place in an implant already in place in a patient's mouth. An impression is recorded of the patient's mouth and the abutment is removed from the mouth, screwed into a laboratory analog of the implant and inserted in the impression. The impression of the patient's mouth is poured with dental stone, the dental stone is separated from the impression and the abutment-containing implant thereby becomes attached to the dental stone model of the patient's mouth. The abutment is then reoriented to fit into the patient's mouth without being seen and to accept a dental prosthesis. The modification may remove some or all of the abutment base. The attaching means and the abutment cuff must not be reoriented. Finally, the reoriented abutment is cast with a dental precious metal which is chemically bonded to the non-oxidizable metal of the reoriented metal abutment. The dental abutment is machinable and is made of a non-oxidizable alloy comprising from 35 to 50 weight percent gold, 15 to 50 weight percent platinum, 15 to 50 weight percent palladium, and 0.1 to 5.0 weight percent iridium.

13 Claims, 1 Drawing Sheet

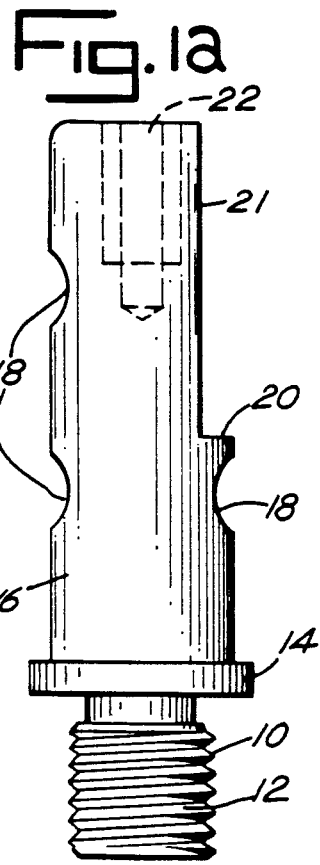
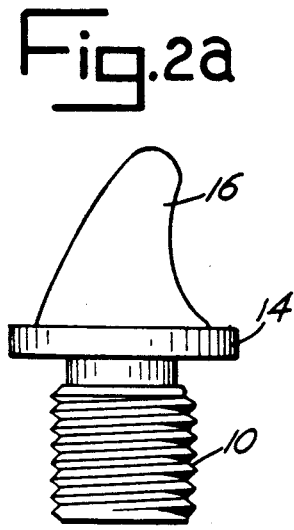
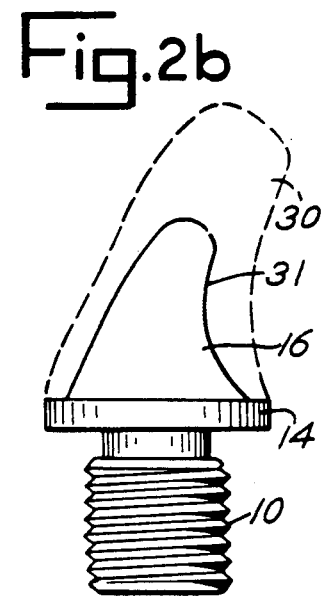
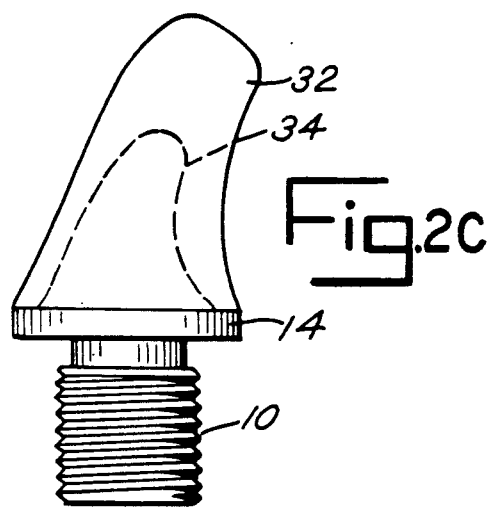
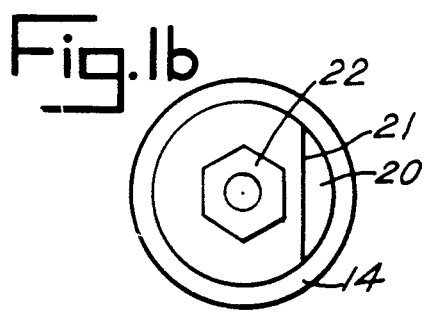
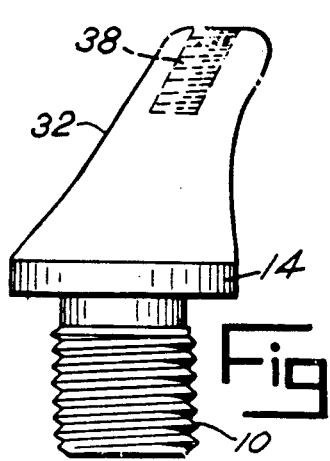
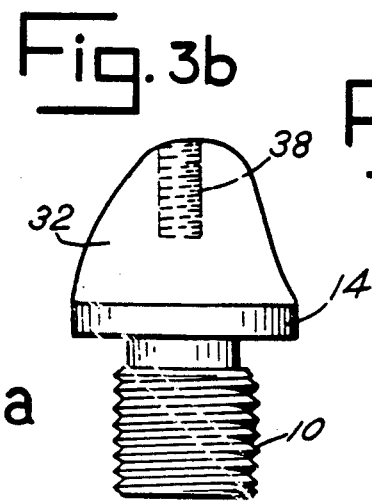
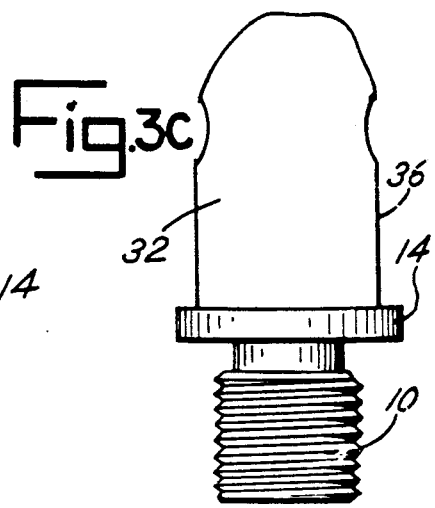

METHOD FOR CONSTRUCTING A CUSTOM ABUTMENT FOR USE IN ASSOCIATION WITH DENTAL IMPLANTS

BACKGROUND OF THE INVENTION

The subject of this invention is a dental abutment, and a method for preparing a custom abutment for use in association with the fabrication of a custom dental prosthesis.

Dental prostheses which are rigidly attached to a patient's jaw using an attaching system consisting of dental implants and abutments are a popular alternative to removable dentures and removable partial dentures. Typical fixed dental prostheses use an implant which is bonded directly to the jaw of the patient, and an abutment which is attached to the implant for uniting the dental prosthesis with the implant. Most implant systems use a two-stage implantation procedure. In the first stage, an implant is installed in the jaw bone of a patient and the site is allowed to heal for a period of three to four months or more. After the implant site has healed and the bone has bonded to the implant, the second stage of the procedure begins. The top of the implant is exposed to view and an abutment is attached to the implant. An impression of the patient's mouth is made and the abutment is allowed to remain in the patient's mouth. An analog of the abutment is inserted into the impression which accurately replicates the abutment. Dental stone (plaster) is poured into the impression and when later separated from the impression, a cast of the patient's mouth is generated with the analog in the position of the abutment in the mouth. The framework for the dental prosthesis is formed around this abutment analog in the dental laboratory using wax or plastic to allow casting of the framework into a dental alloy. The prosthesis will finally be attached to the abutment in the patient's mouth.

A major problem with the dental implant abutment system is that abutments often cannot be oriented to adapt to the installation configurations necessitated by the structure of a patient's mouth. Dental implants are embedded surgically in the jaw bone of the patient. This means that the implant may be angled inwardly or outwardly from the jaw bone depending upon a patient's jaw bone configuration. The problem can be compounded by surgical error. This can be problematical, especially when the implant is embedded in the anterior (front) portion of a patient's mouth in which case the implant often is at a severe outward angle. This angular problem is created because of the length of the abutment protruding beyond the intended tooth contours, or because a retaining screw for the abutment would be visible on the front of the tooth, or because of the creation of problems in permitting a path of insertion of the prosthesis; that is, a misaligned implant is often divergent from other implants or supporting teeth in the mouth making the insertion of the prosthesis impossible.

This problem has been partially solved by offering abutments in pre-manufactured lengths and having pre-manufactured angles. However, such pre-manufactured abutments are not able to be adapted to all patients in all cases. The result of this is that some patients are not presently amenable to the installation of permanent dental prostheses using pre-manufactured abutments.

Presently, abutments are made of titanium, or of a combustible plastic to be cast into a dental alloy. Titanium abutments typically cannot be custom modified by a dentist or technician using available tools. The problem has been addressed by offering titanium abutments in varying lengths and with pre-manufactured angles. Although a titanium post abutment can be slightly reshaped or shortened, one cannot cast additional metal to a titanium post because the outside surface of titanium forms an oxide layer which inhibits any type of molecular bonding between the titanium and the dental alloy. Therefore, such a casted custom modified titanium abutment is prone to breakdown.

Plastic abutments to be cast into dental alloy cannot be fabricated with the accuracy of a machined metal abutment. The threads cannot be machined as accurately and also the resultant interface between the implant and cast abutment is not as accurate. This can produce an abutment with compromised stability. It is possible to add wax and cast to the plastic abutments in the dental laboratory; however, because the threads are plastic and compressible, the rotational position in the cast may be different in the laboratory than in the mouth. Also, because of the difficulties in casting threads accurately, the rotational position prior to casting plastic is usually different than after casting. This can often produce an abutment which appears correctly aligned in the laboratory but is severely misplaced in the mouth.

Therefore, titanium abutments, while being highly machined and capable of being accurately positioned in the patient's mouth, are not amenable to custom modification due the inability of the titanium to chemically or molecularly bond to any alloy that might be used to modify or "cast to" the abutment. On the other hand, plastic abutments, while being capable of some custom modification to conform the abutment to the patient's mouth, are not easily repositioned in the patient's mouth after casting due to the inaccuracy in casting plastic threads. As a result, some patients cannot be fitted with permanent dental prostheses.

SUMMARY OF THE INVENTION

It is, therefore, an object of this invention to provide a method for preparing a custom dental abutment for use in association with dental implants, and for installing a dental prosthesis in the mouth of a patient using a custom dental abutment.

It is also an object of this invention to provide a method for preparing a custom dental abutment that is readily machinable, and that is made of a non-oxidizable alloy which is capable of chemically bonding to a dental precious metal during the casting step of the method.

Finally, it is an object of this invention to provide a custom dental abutment that is machinable that is made with a non-oxidizable alloy, and that is castable with a dental precious metal.

Accordingly, the present invention is a method for preparing a custom dental abutment. The method comprises attaching an abutment comprising a base attaching means, a cuff, and a body and made of a non-oxidizable alloy to a dental implant that is pre-anchored in a patient's mouth. An impression of the patient's mouth containing the abutment is recorded. Next, the abutment is removed from the patient's mouth and attached to a laboratory implant and inserted into the impression. A cast of the patient's mouth is manufactured using the recorded impression such that the laboratory implant containing the abutment becomes attached to the cast of the patient's mouth. The abutment is then reoriented to conform with the configuration of the patient's mouth, existing teeth and the like. Finally, the reoriented abutment is cast with a dental precious metal which bonds to the non-oxidizable abutment alloy to define a custom dental abutment.

In another embodiment, the invention is a method for preparing a custom dental abutment wherein an abutment comprising a threaded base, a cuff and a body is threaded into a dental implant that is anchored in a patient's mouth. The abutment comprises an alloy comprising metals selected from the group consisting of two or more non-oxidizable gold, platinum, palladium, and iridium. An impression of the patient's mouth is recorded preferably with an elastomeric material, while the abutment is installed in the dental implant in the patient's mouth. The abutment is removed from the patient's mouth and attached to a laboratory implant to define an implant assembly. The implant assembly is located in the impression material in the same position and orientation as it was located in the patient's mouth, and a cast of the implant assembly-containing impression is made in dental stone to define a laboratory cast of the patient's mouth. The implant portion of the implant assembly is retained in the laboratory cast. The body of the abutment is then reduced in size as necessary and reoriented with wax or plastic to conform with the aesthetic and structural requirements of the patient's mouth. The reoriented abutment is cast in a dental precious metal to define a custom dental abutment with the dental precious metal being molecularly bonded to the base of the original abutment.

The present invention also includes a dental abutment. The abutment comprises a base attaching means, a cuff, and a body, with the abutment comprising, or more preferably consisting essentially of, a non-oxidizable, machinable alloy.

In another embodiment, the dental abutment of this invention comprises a threaded base, a cuff, and a body. The dental abutment is readily machinable and is made of an alloy comprising, or more preferably consisting essentially of, two or more metals selected from the group consisting of gold, iridium, platinum and palladium.

BRIEF DESCRIPTION OF THE DRAWINGS

Shown in the attached figures is a presently preferred embodiment of the invention wherein like numbers in the various figures refer to like elements and wherein;

FIGS. 1a and 1b show top and front views of the abutment of this invention.

FIGS. 2a, 2b, and 2c show various aspects of the re-orientation of the body of the abutment.

FIGS. 3a, 3b and 3c depict various finished custom dental abutments of this invention.

DESCRIPTION OF THE PREFERRED EMBODIMENTS

The present invention is a method for producing a custom dental abutment, and a dental abutment for use in preparing a custom dental abutment assembly.

The use of a custom dental abutment is appropriate in circumstances where a dental clinician or technician is faced with patient abutment installation limitations such as interocclusal space limitations or a divergence in angulation. In such a case, an abutment will often be angled outwardly due to the shape of the patient's jaw and the location and orientation of the dental implant. It is desirable in such situations to be able to modify the abutment so that the outward angle of the abutment is eliminated. The dental abutment of this invention allows precise control of the desired abutment length, angulation and contour.

The invention is first explained by reference to the figures in which like elements are identified by the same number. FIGS. 1a and 1b show top and front views of an abutment of this invention. The abutment comprises a base attaching means 10, a cuff 14, and a body 16. In this particular embodiment, the base attaching means 10 comprises a threaded male fitting 12 which is complementary to a threaded female fitting of a dental implant. When the abutment is attached to a dental implant by means of the base attaching means 10, the inferior cuff portion acts as a stop to prevent further insertion of the abutment into the dental implant and provides a precise fit of the abutment to the external dimensions of the implant.

The abutment further comprises curved depressions 18, a flat dimension 21 and a shelf 20. When the dental abutment is first attached to a dental implant in a patient's mouth, an impression of the patient's mouth containing the abutment is taken. The purpose of the flat dimension 21 and shelf 20 are to provide a unique profile so that the abutment when attached to a laboratory implant may be inserted into the impression in the exact same orientation as when it was located in the patient's mouth. The depressions 18 allow the abutment to be snapped, or locked into place in the impression as the impression will contain ridges complementary to the abutment depressions 18.

Finally, the abutment comprises a hexagonal keyway 22 in which a tool is inserted to tighten the abutment into place in the dental implant in the patient's mouth. The hexagonal keyway 22 is also used to allow for the removal of the abutment from the patient's mouth after an impression of the patient's mouth has been taken. In the absence of a keyway, a tool may be fabricated engaging the flat dimension 21 of the abutment and encircling the abutment.

FIGS. 2a, 2b and 2c show various aspects of the method for reorienting and customizing the dental abutment of this invention. FIG. 2a is an abutment comprising a base attaching means 10 and a cuff 14 which has been partially reoriented to reduce the size and alter the angle of the abutment body 16. In FIG. 2b, the partially reoriented abutment of FIG. 2a has been further reoriented by adding wax or plastic 30 to the partially reoriented abutment body 16. The abutment of FIG. 2b contains a wax/abutment body interface 31. The wax/abutment body interface 31 is a well-defined interface in which wax could be removed without disturbing the integrity of the abutment body 16.

FIG. 2c depicts a final custom abutment. The custom abutment comprises a base attaching means 10, a cuff 14, and a custom abutment body 32. The custom abutment body 32 includes two distinct alloys commingled at an interface depicted by dashed line 34. The interface depicted by dashed line 34 is not a definite interface. Dashed line 34 merely depicts the location where the alloy which made up the original dental abutment body is intermingled and molecularly attached to the dental precious metal which was cast to the abutment body to produce the custom abutment body 32.

FIGS. 3a, 3b and 3c depict various examples of custom abutments. Every custom abutment will comprise an abutment attaching means 10 and a cuff 14 as it existed in the original dental abutment. In FIGS. 3a, 3b and 3c, however, each abutment body has been reoriented and cast with a dental precious metal to produce a custom abutment body 32. The custom abutment body 32 may be angled as depicted in FIG. 3a, it may be shortened as depicted in FIG. 3b, or it may be customized in any other way necessary to be adapted to a patient's mouth.

FIG. 3c depicts an reoriented abutment in which a portion of the original dental abutment body dimension 36 remains. This is in comparison to the abutments of FIGS. 3a and 3b in which the original dental abutment body dimensions have been obliterated during reorientation. Finally, the custom abutment body 32 may contain a threaded hole 38 as shown in FIGS. 3a and 3b for accepting a screw-type attaching means.

The dental abutment of this invention comprises an attaching means, a cuff, and a body. The abutment is typically generally cylindrical in shape with the attaching means located at one end of the cylinder and the body located at the opposite end of the cylinder from the attaching means, and with the cuff dividing the attaching means from the body.

The attaching means may be any means known in the art which allows the abutment to be securely and reversibly attached to a dental implant located in the mouth of a patient. The attaching means used must be capable of allowing the abutment to be attached and removed from the dental implant a number of times while enabling the abutment to be reattached in the exact same position in the patient's mouth each time the abutment is attached to the dental implant. Therefore, it is preferred that the attaching means be a threaded male fitting that is complimentary to a female threaded fitting in the dental implant. Alternatively, the dental implant may contain a male threaded post, in which case the attaching means of the abutment will be a female threaded fitting. Furthermore, if the implant is threaded with an internal or external locking hex or structural locking feature, the abutment can be structured to engage or to bypass the structural locking feature of the implant. It is important that the attaching means is not reoriented when preparing the custom abutment.

The abutment cuff divides the abutment attaching means from the abutment body. The abutment cuff typically has a slightly larger radius than the abutment body or the abutment attaching means. The purpose of the abutment cuff is to provide a stop for the attaching means. That is, the cuff stops the abutment from being inserted further into the dental implant when the cuff contacts the body of the dental implant. Therefore, the cuff and the attaching means act in unison to insure that the abutment can be reinserted into the dental implant in a patient's mouth in exactly the same position time after time. The inferior portion of the cuff is precisely milled to fit to the superior portion and external dimensions of the implant. Therefor, the cuff insures precise fit of the abutment to the implant. This is important in maintaining health of the surrounding bone and soft tissue of the mouth. Like the attaching means, the inferior dimension of the cuff is not reoriented during preparation of the custom abutment.

The abutment also comprises a body. The dental abutment of this invention has an elongated body. The body is elongated to provide a good profile when an impression is taken of the mouth containing the abutment. The abutment body also must comprise features which allow the abutment to be removed from the patient's mouth and relocated in the impression in the same position as it was located in the mouth. Such features, well known to one of ordinary skill in the art of abutment, may be incorporated in the abutment of this invention.

It is preferred that the abutment contain at least one depression. The depression allows the abutment to be locked in place in a subsequent impression. The depression also allows the abutment to be placed in the impression of a patient's mouth in exactly the same position as it was located when it was first installed in the dental implant in the patient's mouth. It is preferred that the body contain at least one depression running around the entire diameter or part of the diameter of the abutment body. Typically, when creating a custom abutment, the abutment is placed in a patient's mouth and an impression of the mouth is taken. The impression is removed from the mouth and the abutment is removed from the dental implant and located in the impression. The depressions in the abutment will create corresponding ridges in the impression, the result being that the abutment can be snapped into place such that the depression is "locked" into the ridges in the impression. Additionally, it is preferred that the abutment include a flat dimension having a shelf. The purpose of the flat dimension is to provide a keyway in the impression such that the only way the abutment will fit in the impression is to orient it such that the flat dimension of the abutment corresponds to the flat dimension in the impression. In this way, the abutment is always oriented in the impression in a position identical to that it occupied in the mouth. The shelf and the depressions enable the abutment to be laterally oriented in the impression in the proper position. When the abutment is inserted into the impression the shelf and depressions prevent the abutment from being inserted further than the complementary shelf and ridges in the impression. In this way, the abutment is laterally oriented in the mouth in the impression in a position identical to that it occupied.

The abutment of this invention comprised of machinable non-oxidizable alloy comprising two or more metal elements. The metal must be machinable to allow for reorientation of the abutment to produce a custom abutment conforming to the installation requirements of a particular patient's mouth. Additionally, the alloy used in the abutment must be non-oxidizable and relatively non-toxic. An abutment made of a non-oxidizable metal alloy is capable of forming a molecular bond with a dental precious or semi-precious metal which is used to cast the custom abutment. The molecular bond between the abutment body alloy and the cast dental precious metal ensures that the custom dental abutment will not break down at the point where the two metal compositions intermingle. It is preferred that the abutment alloy consist essentially of a non-oxidizable metal alloy.

The preferred non-oxidizable alloy is comprised of two or more non-oxidizable metals selected from the group consisting of osmium, iridium, platinum, gold, palladium, rhodium and ruthenium. It is most preferred that the abutment of this invention is comprised of a metal alloy consisting of two or more metals selected from the group gold, iridium, platinum and palladium. Additionally, it is preferred that the abutment of this invention be comprised of from 15 to 50 weight percent gold, from 15 to 50 weight percent platinum, from 15 to 50 weight percent palladium, and from 0.1 to 5 weight percent iridium. It is most preferred that the dental abutment of this invention be made of an alloy comprising from about 35 to about 45 weight percent gold, from about 25 to about 35 weight percent platinum, from about 23 to about 33 weight percent palladium, and from 0.1 to about 3 weight percent iridium.

Unlike abutments made of titanium, the non-oxidizable metal dental alloy abutment of this invention is readily machinable using tools that are available to a dentist or dental technician. This allows the abutment body to be partially or totally oriented by machining to produce a reoriented dental abutment.

The dental abutment of this invention is used for creating a custom dental abutment. The first step in producing a custom dental abutment is to attach the dental abutment to a dental implant anchored in a patient's mouth. As previously mentioned, this attaching step is preferably accomplished by threading the threaded attaching means of the abutment into a complimentary threaded male or female fitting in the dental implant until the inferior portion of the cuff of the abutment solidly butts against the dental implant. Once the abutment is secure against the dental implant, an impression of the patient's mouth is made with dental impression material. Impression materials such as polyether or polyvinyl siloxane, elastomers, or any other elastomeric or non-elastomeric impression material typically used in dentistry may be used to make an impression of the patient's mouth containing the dental abutment attached to the implant. The impression is allowed to cure or polymerize and is thereafter removed from the patient's mouth.

The dental abutment in the patient's mouth is then removed from the dental implant and attached to an analogous laboratory dental implant to form a laboratory implant assembly. The abutment-containing laboratory implant assembly is then inserted into the dental impression such that the implant assembly is oriented in the impression in exactly the same position in which it was attached to the dental implant in the mouth.

A laboratory cast of the patient's mouth is then created from the implant assembly-containing impression. The cast is prepared by pouring a dental stone or some other dental casting material into the implant assembly-containing dental impression. The cast material is allowed to dry after which the dental cast is separated from the impression material. The dental implant portion of the implant assembly becomes embedded by the dental cast material during this procedure. Therefore, when the dental cast is separated from the impression, the implant assembly comprising the dental implant and the abutment is separated with the dental cast. At this time, any dental stone that is around the abutment cuff can be scraped away and the cuff can be exposed to view. The dental cast can be ditched at this time if desired to simplify modification of the abutment.

The dental abutment is now ready to be reoriented. The abutment at this point is exposed to view and attached to a dental implant embedded in the dental cast material in exactly the same position as it was located in the patient's mouth. Reorientation of the abutment can be accomplished by waxing the abutment, by machining the abutment, or by a combination of both procedures. Typically some portion or all of the abutment body will be removed from the abutment so that a custom abutment having an angled or modified body can be fabricated. During the machining procedure, some to all of the features of the abutment body, including depressions, shelves, flat dimensions, etc., may be obliterated. However, these features of the abutment body are no longer necessary to produce a custom dental abutment.

Once the abutment has been machined as desired, a wax or plastic material may be built up on the remaining portion of the abutment to define the reoriented custom abutment. The exact material used to build up the custom abutment is not critical. Any material used in the dental trade for producing an impression for casting may be used. Typically, a plastic or wax material that is combustible is preferred.

There is now a reoriented abutment of this invention in which the reorientation has been accomplished by machining, waxing or a combination thereof, to define the dimensions of the desired custom dental abutment. The final step to produce the custom dental abutment of this invention is to cast the portion of the custom dental abutment, defined by the built up preferred wax or plastic material, in a dental precious metal. This step is accomplished by techniques known to one of ordinary skill in the art of dental casting. Typically, at this point the abutment will be detached from the implant analog. A casting mold of the wax portion of the reoriented abutment is made. The wax is then removed from the reoriented abutment, and the abutment placed in the cast and then cast in a dental precious metal, or semi-precious metal which becomes molecularly bonded to the non-oxidizable alloy of the abutment to produce a custom dental abutment of this invention. Any dental precious metal or semi-precious metal known in the art is suitable for this casting step.

The custom dental abutment of this invention is now ready for polishing and insertion into the patient's mouth. The custom dental abutment will typically be reinserted into the implant analog in the dental cast and polished and modified as necessary before insertion into the patient's mouth. At this point, the custom abutment can be tapped with a threaded hole to accept a screw-type attaching means, or alternatively, a threaded sleeve defining a threaded hole can be installed in the preferred wax material during reorientation of the abutment body such that when the custom dental abutment is cast in a dental precious metals, the sleeve becomes embedded in the dental precious metal. However, it is not necessary that the custom dental abutment of this invention contain a threaded hole.

The custom dental abutment is now ready to be reinstalled in the patient's mouth. The custom dental abutment is reattached to the dental implant in the patient's mouth such that the inferior cuff portion of the custom dental abutment contacts the dental implant, so that the custom dental abutment is oriented in a position in the patient's mouth identical to the original orientation of the dental abutment. A dental prothesis is finally attached to the custom dental abutment. The dental prosthesis may be attached by a screw-type attaching means if custom dental abutment has a threaded hole. Alternatively, the dental prosthesis may be attached to the custom dental abutment with a medical or dental adhesive. It should be understood that one or more custom dental abutments may be used to retain a dental prothesis in place. When the prosthesis comprises one or two teeth, then a single custom abutment may be enough. However, if the prothesis comprises a plurality of teeth, then two or more custom dental abutments may be necessary to anchor the dental prothesis to the dental implants.

Variations in the structure of the abutment of this invention and in the method for creating a custom dental abutment of this invention will become apparent to those skilled in the art. Any such variations as are within the spirit and scope of this invention are intended to be encompassed within the scope of the claims appended hereto.

Example I

This example details a method for preparing a custom dental abutment for use in anchoring a dental prosthesis to a dental implant located in a patient's mouth.

The first step in the method is to locate a dental implant in the jawbone of a patient such that the implant extends upward towards the patient's gum line.

After complete healing of the gingiva superior to the dental implant, the titanium temporary gingival cuff protecting the implant is removed to expose the superior aspect of the implant body. An abutment consisting of 40 weight percent gold, 30 weight percent platinum, 28 weight percent palladium, and 2 weight percent iridium is screwed tightly in place using a hex wrench. An impression of the patient's mouth is recorded using a conventional elastomeric impression material such as polyether or polyvinyl siloxane.

After the impression is recorded, the abutment is removed from the mouth and threaded firmly into a laboratory implant body analog. This assembly is then inserted into the impression in the same position and orientation as it was located in the mouth. The impression is then poured with dental stone. The laboratory implant body analog becomes embedded in the dental stone allowing the abutment to be located the same position in the cast as in the mouth.

The laboratory cast is pinned and ditched as required to allow for the removal of the assembly from the laboratory cast without unthreading the abutment from the laboratory implant analog. The stone superior to the laboratory implant body analog should be ditched away from the abutment to expose the abutment cuff. The height of the gingiva should be noted to create a supragingival margin unless aesthetics or lack of interocclusal space dictates otherwise. After this preparation of the cast and proper articulation, reorientation of the abutment by waxing the abutment body and/or by machining the abutment body may be accomplished. During reorientation of the abutment, wax (or a combustible plastic) should be added to create the desired custom abutment by beginning at the superior aspect of the cuff. This will maintain the precise fit of the abutment to the implant body. Note that the abutment alloy should not be reduced to a thickness of less than 0.5 mm in order to preserve accuracy in casting procedures.

To aid in precision contour, the waxing may be finished on a milling machine if available or with a surveyor. Once the abutment is properly waxed, it is unthreaded from the implant body analog. Prior to the investing, it should be sprued to the area of greatest wax bulk. The sprue must be at least 3 mm in diameter to prevent cooling of the molten casting alloy before an adequate molecular bond between the abutment and dental precious metal is obtained. After customary burnout, the abutment may be cast in any dental precious metal alloy. Non-precious metal alloys may not be cast to this metal since they will not form a molecular bond with the non-oxidizable abutment alloy.

Following casting, the abutment is threaded back into the abutment body analog in the working cast. The metal is now finished and polished for intraoral try in. Following verification of proper abutment fit, fabrication of the retainer for the prosthesis may be accomplished on the same cast over this custom abutment.

If the hex drive is eliminated from the abutment body during the reorientation of the abutment, a wrench may be fabricated of resin by forcing a "tube" of resin approximately 3 cm long over the finished casting. After the resin is polymerized (autopolymerized or light activated), it is finished to the margins and provides an easy method to thread the casting in place.

Example II

It is often desirable to provide for screw retention of the retainer to be seated over a custom dental abutment of this invention rather than to utilize cement fixation. This may be accomplished on the custom abutment, as produced in the method of Example I by one of two methods. Use of the milling machine permits precise finishing of the metal casting in the laboratory to generate precisely the desired taper and marginal configuration. After external finishing, the milling machine is used to drill and tap a site in the superior (or lingual) aspect of the abutment to fit a pre-made screw.

Alternatively, another technique to create screw retention for the retainer is to incorporate a pre-made "tube and screw" attachment into the wax at the superior aspect of the abutment pattern. The metal sleeve of this pre-made attachment is made of the same type alloy as the metal abutment allowing positive retention into the casting.

I claim:

1. A method of preparing a custom dental abutment comprising the steps of:
   a. attaching an abutment comprising a base attaching means, a cuff, and a body to a dental implant that is anchored in a patient's mouth, the abutment made of a non-oxidizable alloy comprising from 20 to 60 wt % gold, from 15 to 50 wt % platinum, from 15 to 50 wt % palladium, and from 0.5 to 5.0 wt % iridium;
   b. recording an impression of the patient's mouth;
   c. removing the abutment from the patient's mouth, attaching it to a laboratory implant and inserting the abutment attached to the laboratory implant body in the impression;
   d. creating from the impression a laboratory cast of the patient's mouth which retains the abutment and laboratory implant;
   e. reorienting the body of the abutment; and
   f. casting the reoriented abutment with a dental precious metal which molecularly bonds to the non-oxidizable abutment alloy to define a custom dental abutment.

2. The method of claim 1 further characterized in that the base attaching means is a threaded base.

3. The method of claim 1 further characterized in that body of the abutment is reoriented in step (e) by waxing, or by the addition of combustible plastic.

4. The method of claim 1 further characterized in that the body of the abutment is reoriented in step (e) by machining the body of the abutment, followed by waxing the body of the abutment.

5. The method of claim 1 further characterized in that the custom dental abutment is provided with a threaded hole.

6. The method of claim 1 further characterized in that the abutment is reoriented in step (d) by waxing.

7. The method of claim 1 further characterized in that the abutment is reoriented in step (d) by machining.

8. A method for preparing a custom dental abutment comprising the steps of:

a. threading an abutment into a dental implant that is anchored in a patient's mouth, the abutment comprising a threaded base, a cuff, and a body, the abutment made of an alloy comprising gold from 35 to 45 wt % gold, from 25 to 35 wt % platinum, from 15 to 50 wt % palladium, and from 0.1 to 5.0 wt % iridium;
b. recording an impression of the patient's mouth with an elastomeric material;
c. creating a laboratory cast of the patient's mouth by the further steps of:
   i. removing the abutment from the patient's mouth, and threading it into a laboratory implant to define an implant assembly;
   ii. placing the implant assembly in the impression of step (b) in the same position and orientation as it was located in the patient's mouth; and
   iii. casting the implant assembly-containing impression in dental stone to define a laboratory cast of the patient's mouth, the laboratory cast retaining the implant assembly;
d. reorienting the body of the abutment to define a resized abutment; and
e. casting the reoriented abutment of step (d) in a dental precious metal comprising from 20 to 60 wt % gold, from 15 to 50 wt % platinum, from 15 to 50 wt % palladium, and from 0.5 to 5.0 wt % iridium to define a custom dental abutment in which the dental precious metal is molecularly bonded to the reoriented abutment.

9. The method of claim 8 further characterized in that the custom abutment is tapped to accept a threaded attaching means.

10. A dental abutment comprising a threaded base, a cuff, and a body, the threaded base superior to the cuff, and the cuff superior to the body, wherein the abutment comprises from 20 to 60 wt % gold, from 15 to 50 wt % platinum, from 15 to 50 wt % palladium, and from 0.1 to 5 wt % iridium.

11. The dental abutment of claim 10 further characterized in that the base attaching means is a threaded base.

12. The dental abutment of claim 10 further characterized in that the abutment comprises from 35 to 45 wt % gold, from 25 to 35 wt % platinum, from 23 to 33 wt % palladium, and from 0.1 to 3 wt % iridium.

13. The dental abutment of claim 10 further characterized in that dental abutment includes rhodium, ruthenium, or a combination thereof.

* * * * *